United States Patent [19]

Kaupin

[11] 4,066,812

[45] Jan. 3, 1978

[54] FIRE RETARDANT POLYESTER TEXTILE MATERIALS AND METHOD OF MAKING SAME

[75] Inventor: William B. Kaupin, Westwood, Mass.

[73] Assignee: The William Carter Company, Needham Heights, Mass.

[21] Appl. No.: 662,504

[22] Filed: Mar. 1, 1976

Related U.S. Application Data

[63] Continuation-in-part of Ser. No. 556,712, March 10, 1975, abandoned.

[51] Int. Cl.² ............... B05D 1/36; D06M 13/28; D06M 13/32
[52] U.S. Cl. .................. 428/265; 8/DIG. 4; 8/115.5; 427/202; 428/253; 428/287
[58] Field of Search ............. 260/927 R; 8/DIG. 4, 8/115.5, 171; 428/196, 197, 204, 265, 284, 395, 480, 253, 287; 427/197, 202, 203

[56] References Cited

U.S. PATENT DOCUMENTS

| | | | |
|---|---|---|---|
| T916,008 | 8/1971 | Rothwell | 8/171 |
| 3,681,281 | 8/1972 | Jueke et al. | 8/171 |
| 3,775,165 | 11/1973 | Young et al. | 8/171 |
| 3,789,091 | 1/1974 | Anderson et al. | 260/927 R |

*Primary Examiner*—J.C. Cannon

[57] ABSTRACT

Polyester textile materials having improved flammability characteristics even after repeated washings are made by applying thereto an aqueous solution or organic solvent solution containing at least 0.5% by weight of a material having the structure

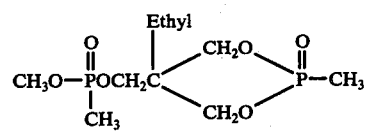

or

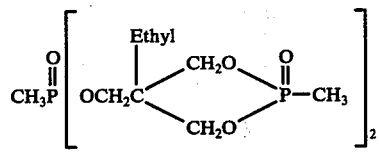

or mixtures thereof, and drying to deposit thereon from 0.5 to 15% of the material by weight. Fabrics, including both 100% polyester fibers and blends with up to 50% by weight of cellulose triacetate fibers containing fire retardant within the fibers, printed with colored designs using conventional pigment colors free from fire retardants also have their flammability characteristics improved by such treatment.

7 Claims, No Drawings

FIRE RETARDANT POLYESTER TEXTILE MATERIALS AND METHOD OF MAKING SAME

This application is a continuation-in-part of application Ser. No. 556,712, filed Mar. 10, 1975, now abandoned.

This invention relates to polyester textile materials having substantially lowered flammability and to a method of making them.

Commercially available flame retarding materials for treatment of polyester textile materials have almost invariably been organic bromine-containing compounds, in some cases containing phosphorus or chlorine as well. Among representative compound of this nature are tris(2,3,-dibromopropyl) phosphate, tris(dibromophenyl) phosphate, di(2,3-dibromopropyl) tribromophenyl phosphate, pentabromochlorocyclohexane, hexbromocyclohexane, hexabromocyclododecane, tris(2,3-dibromopropyl) trimellitate, tribromophenol, tetrabromophenol, tetrabromobisphenol-A, ethylene oxide adduct of TBBA-A, pentabromophenol, pentabromophenyl acetate decabromodiphenyl oxide, tetrabromovinylcyclohexene, pentabromoethylbenzene, hexabromobenzene, pentabromotoluene, tetrabromonaphthalene, hexabromonaphthalene, tetrabromophthalic anhydride and dimethyl tetrabromophthalate. Such compounds are extremely insoluble in water and must be applied to textile materials either in the form of a solution in an organic solvent, a procedure which is expensive and requires special equipment, or in the form of an aqueous dispersion, in which case they are readily removed from the textile by ordinary washing. In either case the treated textile material has in most cases an objectionable oily or greasy hand. Indeed, in the case of the widely used tris(2,3-dibromopropyl) phosphate, the material is employed in the form of an aqueous dispersion of a solvent solution because of the difficulty of preparing a stable aqueous dispersion of the phosphate itself.

In order to achieve durability to washing, it has been proposed to heat the textile materials in contact with the water-insoluble compounds (whether applied from organic solvent or aqueous dispersion) at elevated temperatures of the order of 375° to 410° F. for a period of 30 to 95 seconds to cause the compounds to diffuse into the substance of the polymer which forms the fibers. While this step improves durability of the fire retardant effect, it does not eliminate the oily or greasy hand and it has the undesirable effect of imparting stiffness and boardiness to the textile material, necessitating an aqueous alkaline afterwash at high temperature to soften the hand. The afterwash is ineffective to eliminate completely the oily or greasy hand, and the treated textile material not only displays a greyish or yellowish discoloration immediately after treatment but, even more seriously, it exhibits a tendency to become further discolored by accumulation of embedded soil and dirt during use to a greater extent and more rapidly than untreated textile material of the same fiber content.

The problem of retarding flammability is particularly acute in the case of textile fabrics woven from polyester fibers or from blends of polyester fibers with cellulose triacetate fibers used for children's sleepwear for which flammability standards have been established. Even when there is used in such blends a cellulose triacetate fiber which contains approximately 14–15% by weight of tris(2,3-dibromopropyl) phosphate incorporated in the melt from which the fibers are spun, as is the case with the cellulose triacetate fibers sold under the name FR Arnel, the blend requires additional treatment to meet the established flammability standards. Furthermore, even after the polyester fabric, whether it be 100% polyester or the aforesaid blend, has been treated with any of the usual water-insoluble fire retardant materials, the fabric cannot be subsequently printed with conventional pigment printing pastes without adversely affecting its flammability characteristics, nor can lace or other trim materials be applied to garments made from such fabrics without such effect; in those cases, it is now necessary to employ additional flame retarding material, incorporating it, for example, directly in the printing paste. Consequently, printed areas of the fabric as well as the unprinted areas present a dull and dingy appearance.

Although it has been proposed to employ certain watersoluble cyclic phosphonate esters as flame retardant agents for polyesters, the only procedure suggested for using them has been direct blending of the water-soluble materials into the molten polymer either prior to or during formation of the fibers, as described in Anderson et al. U.S. Pat. No. 3,789,091 issued Jan. 29, 1974.

It has now been found that essentially permanent flame retardant properties are imparted to polyester textile materials by topical application of a water solution or organic solvent solution, free from print binder, of certain water-soluble cyclic phosphonate esters. The treatment provides remarkably improved flammability characteristics and can be carried out using a water solution, as is preferred, without the necessity of employing any organic solvents or emulsions; and despite the initial water solubility of these esters, they remain in place on the textile material in sufficient quantity to provide effectively improved flammability characteristics ever after 50 successive washing operations while at the same time providing a product having greatly improved whiteness and softness of hand free from an oily or greasy feel without resort to afterwashing. Textile materials treated in accordance with the present invention are found to improve further in whiteness after successive washings rather than becoming worse. Practice of the invention is compatible with equipment commonly found in any fabric finishing plant, namely a padder and dryer.

It has been found that pigment printing pastes and the print binders they contain interfere with the operation of the present invention under certain circumstances. If the polyester fabric is printed with the pigment printing paste before topical application of the water-soluble cyclic phosphonate ester flame retardant, the print pattern, which penetrates into the fabric up to 50% or more of the fabric thickness, forms an impermeable coating which is locked to the fabric and which effectively prevents access of the flame retardant solution to the polyester textile material or fabric except in the unprinted areas; the fabric in the printed areas is shielded from direct contact with and complete saturation by the solution of flame retardant because of the presence of the print binder in those areas. The flame retardant left on the surface can readily be washed off the pigment print areas after drying and provides little or no fire- or flammability-resistance for these areas after washing. If the total area covered by the pigment print is only a small fraction of the total fabric area, up to about 30%, the aqueous solution of cyclic phosphonate ester fire retardant may be effectively applied after pigment printing of the fabric to achieve a high degree of washdurable fire- or flammability-resistance overall, but the degree of effectiveness gradually decreases as the proportionate area covered by the pigment print increases because of the shielding effect of the pigment print and its print binder.

It has also been found that the water-soluble cyclic phosphonate ester flame retardant cannot be effectively applied simultaneously with pigment printing by dissolving the flame retardant in the aqueous portion of the pigment printing paste. None of the conventional pigment print binders tested has been found useful to retain the effectiveness of the water-soluble flame-retardant after washing when applied in this manner. The exact reasons for this phenomenon are not fully understood, but apparently the presence of the print binder or some other property or characteristic of the pigment print paste prevents direct contact of the water-soluble flame retardant with the polyester fabric or the polyester fibers thereof.

Once a polyester fabric has been treated with the water-soluble flame retardant of the present invention by direct contact with an aqueous solution and dried at a temperature of at least 250° F., subsequent pigment printing with a pigment print paste does not appreciably affect the wash-durable flame-resistance of the fabric. In the case of fabrics previously treated with water-soluble flame retardant in accordance with the present invention, it appears that the inherent flammability of the print binder present on the fabric is overcome by the flame retardant present in the fabric, even when the pigment print area is 100% of the total area of the fabric (one side only), so that the present invention provides wash-durable flammability resistance characteristics both for 100% polyester fabrics and for fabrics made from blends of polyester fibers with cellulose triacetate fibers if the fabric is treated in accordance with the invention whether or not the fabric is subsequently printed with a pigment print paste. This is true even when the pigment print paste itself contains no added flame-retardant, either water-soluble or water-insoluble, and when the pigment print area is as high as 30-100% of the total area of the fabric (one side only), and is in marked contrast to the substantial decrease in flammability resistance of the overall fabric brought about by the use of such pigment print pastes on polyester fabric previously treated with any of the usual water-insoluble flame retardant materials.

Wet printing or disperse dye printing of the polyester fabric, on the other hand, does not interfere with the present invention, and wet printing can be carried out either before or after topical application of a water solution of the water-soluble flame retardants of the present invention without appreciable effect upon the wash durability of the flammability resistance of the fabric. Furthermore, the water-soluble flame retardant can be dissolved in the aqueous print paste used for wet printing or disperse dye printing, which paste contains no print binder, and applied effectively to the fabric during the printing operation to provide wash-durable flammability resistance for the print areas. Whether such a procedure by itself provides effective wash-durable flammability resistance for the overall fabric, that is, the fabric as a whole, depends upon the extent of print coverage, decreasing as the extent of coverage decreases from 100%. Because no print binder having inherent flammability is added to the fabric during wet printing or disperse dye printing, effective flammability resistance is achieved by the foregoing procedure in one-side printing even when the extent of coverage is fairly low, but this mode of practicing the invention is not preferred when the wet print coverage is less than about 30% of the total fabric area, in the case of lightweight fabrics, or less than 50% of the area in the case of heavyweight fabrics. The steaming or thermosoling step conventionally used at the conclusion of the wet-printing process is effective for causing the water-soluble flame retardant to become permanently affixed to the polyester fabric. Moreover, in the continuous dyeing of polyester fabrics by padding with disperse dye and drying, then steaming or thermosoling to provide permanency to washing, the flame retardant of the present invention can be simultaneously applied simply by adding it to the dye bath.

The present invention provides a method of treating polyester textile materials to increase their fire-resistant or flammability-resistant characteristics which comprises applying directly thereto a solution, either in water or an organic solvent, free from print binder and containing at least 0.5% by weight of a material selected from the group consisting of those having the structures

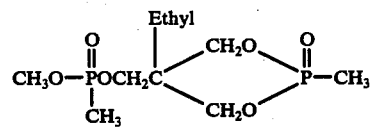

and

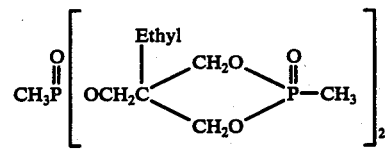

and mixtures thereof, and drying at a temperature of at least 250° F. to deposit on said textile material from 0.5 to 15% of said material by weight. It has been found that the minimum amount of the foregoing cyclic phosphonate esters which is required for effectiveness in flame retardancy is much less than the minimum amount required of conventional bromine-containing flame retardants such as tris(2,3-dibromopropyl) phosphate.

The cyclic phosphonate esters employed in the present invention as set forth above can be prepared as described in Anderson et al. U.S. Pat. No. 3,789,091. The polyester textile material which can be treated in accordance with the present invention contains a polyester such as poly(ethylene terephthalate) or poly(1,4-cyclohexylenedimethyleneterephthalate); it can be in the form of mono-filaments, staple fibers, or of yarns or threads, as well as woven and non-woven fabrics, knitted fabrics, and tufted carpeting, and the term "textile material" is intended to include all of these forms. However, the invention finds its greatest utility in the treatment of knitted or woven fabrics made from such polyester. These fabrics may vary in weight over a wide range, those from 4 to 10 oz. per square yard being of greatest commercial importance for wearing apparel. While the invention is of great value as applied to fabrics used in wearing apparel, it is also valuable in upholstery fabric and carpeting which may weigh as much as 25 oz. per square yard. It has been found that in order to apply an effective amount to a textile material in a single operation, the aqueous or solvent solution employed should contain at least 0.5% by weight of the ester, the remainder being water or solvent. It may contain up to 15% by weight of the ester or even more, but ordinarily there is no advantage in employing much higher concentrations, although a higher concentration does no harm. The textiles which can be effectively treated in accordance with the present invention include not only those consisting of 100% polyester fibers but also those which are made from blends of polyester fibers with up to 50% by weight (based on the total textile weight) of cellulose triacetate fibers, which cellulose triacetate fibers are spun from a melt containing 10-15% by weight of tris(2,3-dibromopropyl) phosphate such as that sold under the name FR Arnel.

The water-soluble flame retardants, after application to the polyester textile material in accordance with this invention, cannot be completely removed by ordinary washing, and they provide effective flammability resistance even after 50 washings. The reason for the apparent loss of water solubility after application to the polyester textile material and drying is not fully understood.

The solution of flame retardant in water or solvent can be applied to the textile material such as fabric or tufted carpet using processes and equipment conventionally employed in the textile industry with no problem of corrosion of equipment; for example, it can be applied by spraying or padding, by a roll-wipe process or by engraved rollers, the pick-up being adjusted in each case to provide a deposit of the specified cyclic phosphonate ester material amounting to 0.5 to 15% by weight of the polyester after drying. Organic solvents which can be used include acetone, ethanol, ethylene chloride, perchlorethylene, 1,1,1-trichloroethane, benzene and similar materials. Solutions in water are preferred.

The present invention can be employed with polyester textile materials which are 100% polyester as well as with those which contain blends of polyester with other fibers such as cellulose triacetate or cotton. While the invention has little or no effect on the flame-resistance of the cellulose triacetate or cotton portion of the blend, it does have a substantial effect on the flame resistance of the blend as a whole, particularly when the blend contains 75% or more by weight of polyester. One commonly used fabric contains a blend of polyester fibers with an equal weight of cellulose acetate fibers, which cellulose triacetate fibers are spun from a melt containing approximately 15% by weight of tris(2,3-dibromopropyl) phosphate, sold under the name FR Arnel. Such a blended fabric is incapable of meeting the Federal Standard for the Flammability of Children's Sleepwear as defined hereinafter, but the present invention does enable such a fabric to meet this standard, as well as similar blended fabrics containing less than 50% by weight of FR Arnel.

Drying of the textile material after treatment with the aqueous or solvent solution of the phosphonate ester can also be carried out on conventional equipment such as loop, cage drum, suction drum or tenter frame dryers and under conditions usually employed. Heating in hot air at temperatures of 250° F. and upward, preferably 340° F. or more, is all that is required. Usually heating for two minutes in hot air at the minimum temperature is enough to obtain complete dryness, but heating for a further period of 15 seconds at a higher temperature may be employed. Heating at temperatures higher than the minimum appears to increase the amount and/or effectiveness of the flame retardant remaining on the fabric after washing; the use of higher temperatures and/or longer times is particularly desirable in the case of heavier fabrics. The only upper limit on the temperature used is that which is imposed by damage to the textile material. Heating in hot air or on a tenter frame or on heated rollers is preferred in order to minimize costs; temperatures as high as 380° F. or even higher can be employed as in heat setting in the case of textile materials made of 100% polyester fibers. In the case of heavy fabrics or napped fabrics the use of temperatures above 340° F., as in thermosoling, a step which sometimes is used to enhance diffusion of dyes or other materials into the substance of the fibers, is preferred. However, in the case of blends of polyester fibers with cellulose triacetate fibers, the temperature usually need not exceed 340° F. The precise times and temperatures employed, as well as the precise amount of water soluble phosphonate ester used for best results in any given case will depend upon the construction and weight of the fabric as well as upon the nature of any dyeing or printing and even the design of the ultimate garment or other article made from the treated fabric. Sleepwear garments decorated with various trims, laces, and embroidered or sewn designs and garments made with smocking require that the fabric be treated with larger quantities of the water-soluble flame retardant than do plain garments in order to achieve equivalent results. For example, in the case of plain garments made from white lightweight (3-4 oz./sq.yd.) polyester fabric, excellent results are achieved using 2% or more of the water-soluble phosphonate ester based on the weight of the fabric, while in the case of a garment made of heavyweight (7-8 oz./sq.yd.) knitted and napped polyester fabric, a larger amount, of the order of 4% by weight based on the weight of the fabric, is required for equivalent flammability characteristics. In the case of heavyweight napped fabrics, it is preferred for best results to heat the fabric, after bringing it into direct contact with the aqueous or solvent solution of the water-soluble flame retardant, at a relatively low temperature, about 220° to 250° F., in order to minimize migration of the flame retardant to the napped surface, then heat the fabric further at a temperature of 340° to 370° F. for approximately 20 seconds.

The effect of the present invention in increasing the flammability or fire resistance of textile materials can be demonstrated by a standard test such as DOC FF 3-71, the Standard for the Flammability of Children's Sleepwear published at 36 Federal Register 14062-14073 (1971) as amended July 29, 1973. Pigment printed fabrics made of 100% polyester which contain no flame retardant are incapable of meeting the minimum requirements of this test, as are blended fabrics such as those containing FR Arnel, but after treatment in accordance with the present invention they are capable of meeting these requirements. The foregoing standard requires the use of 50 washes or launderings to which the fabrics are subjected in the course of the test; the standard does not require the use of a bleach in the washing, but it has nevertheless been found that polyester fabrics treated in accordance with the present invention will withstand the more severe test of 50 successive washes even when a bleach such as Clorox is added to the wash water and will continue to meet the test standard. The presence of the cyclic phosphonate esters affixed directly to the polyester textile material and durable to washing can be shown not only by the foregoing standard flammability test but also by chemical analysis of the textile material for phosphorus content. Such analyses show that after removal of excess flame retardant during the first wash, the amount of flame retardant remaining affixed to the polyester continues virtually undiminished in amount during 50 washes.

The following specific examples are intended to illustrate more fully the nature of the invention without serving as a limitation upon its scope.

EXAMPLE 1

A scoured, white, 10 cut, heavyweight jersey fabric single knit (19 stitches to the inch) from 8/1's CC Fortrel 310 yarn [100% poly(ethylene terephthalate)] weighing 7.5 oz. per square yard suitable for making children's sleepwear was padded to a pickup of 102% with an aqueous solution containing as flame retardant 7.0% by weight of a mixture (85:15 by weight) of two cyclic phosphonate esters having the structure

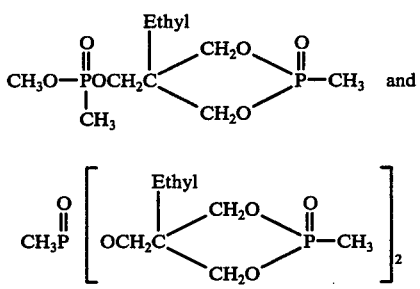

as described in U.S. Pat. No. 3,789,091 and sold under the name Antiblaze 19. The wet fabric was dried in hot air at 260° F., then heated on a pin frame at 380° F. for 90 seconds in order to stabilize or heat set the fabric.

The procedure did not adversely alter any properties of the polyester fabric substrate. The treated fabric was only very slightly less lustrous and white than the original fabric and the hand was very soft and free from any greasy or oily feel. Consequently, there was no necessity for any afterwash.

Samples of the treated fabric and the untreated (control) fabric were tested in accordance with the Standard for the Flammability of Children's Sleepwear DOC FF 3-71 (as amended). Fifteen specimens, seamed in each fabric direction, were used instead of the five required by the standard. All specimens were merrow seamed, 14 stitches/inch, with regular 100/2 ticket spun polyester thread (not treated with flame retardant).

The untreated control fabric showed 2 failures from 15 specimens seamed in the length direction and 6 failures from 15 specimens seamed in the width direction, the failures in each case being caused by excessive residual flame time.

Thirty specimens of treated fabric tested before and after 50 washings showed "Zero Burn", meaning that each of the 15 specimens seamed in the length direction and each of the 15 specimens seamed in the width direction extinguished burn immediately upon retraction of the test flame. A most extraordinary effect was that all test specimens, at the ignited areas showed a white polymer melt only, i.e., there was no smoke, blackening or dripping of the polymer melt. The char lengths for the treated fabric were as follows:

|  | 15 Specimens Seamed in Length | 15 Specimens Seamed in Width |
|---|---|---|
| Treated Fabric | 0.8 – 1.2 inches ave. 1.0 inch | 0.9 – 1.0 inches ave. 1.0 inch |
| After 50 Washings | 0.8 – 1.0 inches ave. 0.9 inch | 0.7 – 1.0 inches ave. 0.8 inch |

The whiteness of the fabric after 50 washings was excellent. In fact, it was whiter than the original treated fabric due to inherent development of a blue tinge which functions like an optical brightener.

EXAMPLE 2

The same fabric described in Example 1 was in actual mill process open width padded with a pickup of 52% with an aqueous solution containing 17% by weight of the same mixture of phosphonate esters as in Example 1. The wet fabric was simultaneously dried and heat set at 380° F. in a three section Fab-Con Tenter Dryer. The amount of flame retardant was 8.9% on dry fabric weight. After drying, the treated fabric and, for comparison, a sample of scoured untreated control fabric, were open width printed with conventional oil phase pigment colors (no flame retardant additives in the print paste) in an awning design with 90% print coverage. After printing, both the treated and untreated control fabric were tested in accordance with Federal Standard DOC FF 3-71. In flammability tests on each fabric, 30 seamed specimens were tested as in Example 1.

The untreated control fabric tested after printing showed consistent failure to meet both char length and residual flame time criterions. After 50 washings, 20 specimens from 30 specimens of control fabric tested failed to meet the residual flame time criterion.

The treated fabric tested after printing easily passed the Federal Standard for flammability both before washing and after 50 washings of the fabric. The test results were as follows:

|  | 15 Specimens Seamed in Length | 15 Specimens Seamed in Width |
|---|---|---|
| Original Fabric (after printing) |  |  |
| Char Length (Inches) | 1.0 – 1.3 ave. 1.2 | 0.9 – 1.4 ave. 1.1 |
| Residual Flame Time (Seconds) | 0 | 0 |
| After 50 Washings |  |  |
| Char Length (Inches) | 0.9 – 1.2 ave. 1.1 | 0.8 – 1.2 ave. 1.1 |
| Residual Flame Time (Seconds) | 0 | 0 |

In vertical flame tests of the treated fabric after printing, each of the 30 seamed specimens tested extinguished burn in 2 seconds, or less, after flame retraction. In the vertical flame test of the treated fabric after 50 washings, 3 specimens from 30 specimens tested had self-extinguishing drips of 4, 5 and 6 seconds, respectively. The remaining specimens extinguished burn immediately upon flame retraction.

EXAMPLE 3

In actual mill process, a scoured, white, 22 cut, jersey fabric single knit (30 stitches per inch) from 20/1 CC Fortrel 310 yarn (100% polyethylene terephthalate) weighing 4.8 oz. per square yard was tubular padded to a pickup of 68% with an aqueous solution containing 5% by weight of the same phosphonate ester mixture as in Example 1. The wet fabric was tubular dried in a two section Tubetex Dryer. The first section of the dryer was steam heated and the second section was gas fired. The temperature of the fabric in the first section did not exceed 220° F. and in the second section did not exceed 340° F. as measured by thermal sensitive papers attached to the fabric. The dwell time of fabric in the dryer was 90 seconds. There was no perceptible odor during the pad and dry operations. After drying, the treated polyester had a very soft hand and was lustrous and bright white in color. It was completely free of odor or any oily or greasy feel. Consequently, an after-wash was not required. The content of flame retardant was 3.4% on dry fabric weight. After washing, the content of flame retardant on dry fabric weight decreased to 1.7%.

The treated tubular fabric and, for comparison, a sample of scoured untreated (control) fabric were slit and open width printed with conventional oil phase pigment colors (no flame retardant additives in the print paste) in a pattern with 35% area coverage. The printed fabric was dried and cured at a temperature of 260° F.

Treated and control fabrics after printing were tested for fabric flammability in accordance with Federal Standard DOC FF 3-71 using 30 specimens of each as in Example 1.

From the control (untreated) fabric tested after printing and before washing, there were 8 failures from 15 specimens seamed in the length direction and 8 failures from 15 specimens seamed in the width direction. After 50 washings there were 4 failures from 15 specimens seamed in the length direction and 4 failures from 15 specimens seamed in the width direction. In every case failures were the result of excessive residual flame time.

The treated fabric tested after printing and after 50 washings easily passed the Federal Standard test. The results were as follows:

|  | 15 Specimens Seamed in Length | 15 Specimens Seamed in Width |
|---|---|---|
| Original Fabric (after printing) | | |
| Char Length (Inches) | 1.3 to 2.3 ave. 1.8 | 1.7 to 2.0 ave. 1.8 |
| Residual Flame time (Seconds) | 0 | 0 |
| After 50 Washings | | |
| Char Length (Inches) | 1.5 to 1.9 ave. 1.7 | 1.6 to 2.0 ave. 1.8 |
| Residual Flame time (Seconds) | 0 | 0 |

In the vertical flame test on treated fabric after printing and before washing, there was one self-extinguishing drip (SED) at 6 seconds from 15 specimens seamed in the length direction and one SED at 2 seconds from 15 specimens seamed in the width direction.

In the vertical flame test on treated fabric after 50 washings, each of the 15 specimens seamed in the length direction extinguished burn immediately upon retraction of the flame. From 15 specimens seamed in the width direction, two specimens had an SED at 2 and 3 seconds, respectively.

An additional 30 specimens were subjected to a still more severe test by substituting in the usual washing procedure of the Federal Standard a wash liquid consisting of water containing one cup of Tide detergent and one cup of Clorox bleach for each 6 lb. of wash load. After 50 such washings, the test results were as follows:

|  | 15 Specimens Seamed in Length | 15 Specimens Seamed in Width |
|---|---|---|
| Char Length (Inches) | 1.4 to 2.0 ave. 1.7 | 1.4 to 1.9 ave. 1.7 |
| Residual Flame time (Seconds) | 0 | 0 |

All of the specimens seamed in length exhibited "Zero Burn"; of the 15 seamed in width, only two had self-extinguishing drips of 3 and 6 seconds respectively, the remainder all extinguishing immediately upon retraction of the flame.

EXAMPLE 4

To illustrate the negligible effect that the flame retardant finish has on esthetic properties of the polyester fabric, another length of the fabric described in Example 3 was, in actual mill process, treated with amounts of flame retardant far in excess of the amount necessary to impart permanent flame retardance. One roll of fabric was tubular padded to a pickup of 72% with an aqueous solution containing 10% by weight of Antiblaze 19. The content of flame retardant chemical was 7.2% on dry fabric weight. Another roll was tubular padded to a pick-up of 86% with an aqueous solution containing 15% by weight of Antiblaze 19. The content of flame retardant chemical was 12.9% on dry fabric weight. The procedure for drying and printing was identical to that given in Example 3. In fact, all fabrics were dried and printed in the same mill run.

By appearance and tactual evaluation, it was virtually impossible to distinguish any difference between the printed control (untreated) fabric and printed fabrics treated as in Example 3 or this Example at levels of 3.4, 7.2 and 12.9% of flame retardant. All treated fabrics had the same high lustre, bright whiteness and brilliancy of print. The whiteness as measured by a Photovolt Reflection Meter, Model 670 was as follows:

| Fabric | Reflectance |
|---|---|
| Control | 100 |
| 3.4% flame retardant | 96 |
| 7.2% flame retardant | 95 |
| 12.9% flame retardant | 94 |

EXAMPLE 5

In actual mill process, another length of the fabric described in Example 3 was open width padded to a pickup of 61% with an aqueous solution containing 10% by weight of Antiblaze 19. The wet fabric was dried in a three section Fab-Con tenter dryer at a temperature of 340° F. at a dwell time in the dryer of 80 seconds. The content of flame retardant was 6.1% on dry fabric weight. After drying, the treated fabric was open width printed with conventional oil phase pigment colors (no flame retardant additives in the print paste) in an awning design with 90% print coverage. After printing, the fabric was heat set by tentering at 380° F. for 50 seconds.

The treated and printed fabric was tested for fabric flammability in accordance with Federal Standard DOC FF 3-71, using 30 specimens seamed as described in Example 1. It easily passed the Federal Standard for flammability both before washing and after 50 washings. The test results were as follows:

|  | 15 Specimens Seamed in Length | 15 Specimens Seamed in Width |
|---|---|---|
| Original Fabric (after printing) | | |
| Char Length (Inches) | 1.5 to 2.0 ave. 1.7 | 1.5 to 2.0 ave. 1.8 |
| Residual Flame Time (Seconds) | 0 | 0 |
| After 50 Washings | | |
| Char Length (Inches) | 1.5 to 1.8 ave. 1.6 | 1.5 to 1.9 ave. 1.8 |
| Residual Flame Time (Seconds) | 0 | 0 |

In the vertical flame test on treated fabric after printing, each of the 15 specimens seamed in the length direction extinguished burn immediately upon retraction of the flame. From 15 specimens seamed in the width direction, only one specimen had a self-extinguishing drip at 2 seconds.

In the vertical flame test on treated fabric after 50 DOC 3 washings, there was one SED at 5 seconds from 15 specimen seamed in the length direction and one SED at 3 seconds from 15 specimens seamed in the width direction.

EXAMPLE 6

A scoured, white, 10 cut, heavyweight jersey fabric single knit, 19 stitches to the inch, with 8.5/1' s CC yarn comprised of a 50/50 blend of FR Arnel (cellulose triacetate)[1] and Fortrel 310 (polyester) fibers weighing 7.0 oz. per square yard was padded at a pickup of 98% with an aqueous solution containing 5% by weight of Antiblaze 19. The wet fabric was dried at 240° F., and heat set at 340° F. for 2 minutes in order to stabilize the fabric to wash shrinkage. The content of flame retardant in the treated fabric was 5% on dry fabric weight, 2.5% on polyester.

[1] FR Arnel has 14% by weight of tris(2,3-dibromopropyl) phosphate melt incorporated before spinning the fiber.

The treated fabric and a sample of untreated (control) fabric were roller printed with conventional oil phase pigment colors (no flame retardant additives to the print paste) in a floral design with 70% area coverage.

The treated fabric and untreated control fabric were tested in accordance with Federal Standard DOC FF 3-71, using 30 specimens of each seamed as described in Example 1.

The untreated control fabric tested after printing and before washing showed that 22 specimens from 30 specimens tested failed to meet the residual flame time criterion.

The treated fabric tested after printing and before washing showed "Zero Burn". Each of the 30 seamed specimens tested extinguished burn after retraction of the test flame.

EXAMPLE 7

The same fabric described in Example 1 was padded with a pickup of 100% with an aqueous solution containing 8% by weight of the same mixture of phosphonate esters as in Example 1. The wet fabric was dried by placing it on a pin frame in a laboratory hot air oven at 260° F. for approximately two minutes. After drying, the treated fabric resembled that of Example 1 in appearance and hand. A sample of the treated fabric and a sample of untreated control fabric were tested for flammability as described in Example 1. The treated fabric before washing passed the test exhibiting "Zero Burn". After 50 washings the treated fabric also passed; in the vertical flame test, five specimens from a total of 30 tested had self-extinguishing drips of 3 to 4 seconds each, the remainder displaying extinction of burn immediately after flame retraction. In contrast, the control fabric after 50 washings showed three failures from 15 specimens seamed in the length direction and three from 15 seamed in the width direction, the failures in each case being caused by excessive residual flame time, i.e., more than 10 seconds.

The test results for the treated fabric were as follows:

|  | 15 Specimens Seamed in Length | 15 Specimens Seamed in Width |
|---|---|---|
| Original | | |
| Char Length (Inches) | 0.8 to 1.1 ave. 0.9 | 0.8 to 1.2 ave. 0.9 |
| Residual Flame time | 0 | 0 |
| After 50 Washings | | |
| Char Length (Inches) | 0.7 to 1.4 ave. 1.0 | 1.1 to 1.3 ave. 1.2 |
| Residual Flame time (Seconds) | 0 | 0 |

EXAMPLE 8

The identical fabric used in Example 1 was sprayed with an aqueous solution containing 20% by weight of the same mixture of cyclic phosphonate esters as in Example 1 and in addition 0.5% by weight of surfactant octyl phenoxy polyethoxy (9-10) ethanol (Triton X-100) to facilitate penetration of the spray solution into the fabric. The solution applied to the fabric amounted to 20% by weight, depositing 4% flame retardant chemical on the polyester fabric. The sprayed wet fabric was dried in hot air at a temperature of 260° F., then heated on a pin frame at 375° F. for 90 seconds in order to heat set the fabric. The treated fabric showed excellent retention of whiteness and had a smooth, soft hand, so that no afterwash was necessary.

Fifteen samples of the treated fabric were Merrow seamed with regular 100/2 ticket spun polyester thread in the width direction, the most flammable direction, and tested for flammability in accordance with the DOC FF 3-71 specification as described in Example 1. All seamed specimens showed "Zero Burn" both before and after the 50 washings. The char lengths of the 15 specimens tested after 50 washings averaged 0.9 inch and the range was 0.8 to 1.1 inches.

Fifteen specimens of control untreated fabric were seamed and tested in the same way for fabric flammability. After 50 washings, the control fabric showed 3 failures from 15 specimens tested, the failures in each case being caused by residual flame time.

EXAMPLE 9

The same fabric described in Example 1 was in actual mill process padded in tubular form to a pickup of 56% with an aqueous solution containing 10% by weight of the same cyclic phosphonate ester mixture as described in Example 1. The wet fabric was tubular dried in a two section Tubetex dryer. The first section of the dryer was steam heated and the second section was gas fired. The temperature of the fabric in the first section did not exceed 220° F. and in the second section did not exceed 340° F. as measured by thermal sensitive papers attached to the fabric. The dwell time of the fabric in the dryer was 90 seconds. There was no perceptible odor during the pad and dry operations. After drying, the treated polyester fabric had a soft, desirable hand and was lustrous and white in color. It was completely free of odor or any oily or greasy feel; consequently, an afterwash was not required. The amount of flame retardant applied by padding was 5.0% by weight of the fabric, but after one washing the amount fixed on the fabric as determined by analysis for phosphorus content of the treated fabric was 2.9% by weight; after 50 washings, analysis showed the phosphorus content to be virtually unchanged.

The treated tubular fabric and, for comparison, a sample of scoured untreated (control) fabric were slit and open width printed with conventional oil phase pigment colors (no flame retardant additives in the print paste) in a pattern with 35% total area coverage. The printed fabric was dried and cured at a temperature of 260° F. Treated and control fabrics after printing were tested for fabric flammability using 30 specimens of each as in Example 1.

From the control (untreated) fabric tested after printing and before washing, there were 3 failures from 15 specimens seamed in the length direction and 2 failures from 15 specimens seamed in the width direction. After 50 washings there were 2 failures from 15 specimens seamed in the length direction and 1 failure from 15 specimens seamed in the width direction. In every case failures were the result of excessive residual flame time.

The treated fabric easily passed the test both before and after washing. The results were as follows:

|  | 15 Specimens Seamed in Length | 15 Specimens Seamed in Width |
| --- | --- | --- |
| Original Fabric (after printing) | | |
| Char Length (Inches) | 0.9 – 1.2 ave. 1.1 | 1.0 – 1.3 ave. 1.2 |
| Residual Flame Time (Seconds) | 0 | 0 |
| After 50 Washings | | |
| Char Length (Inches) | 0.9 – 1.2 ave. 1.1 | 0.9 – 1.3 ave. 1.1 |
| Residual Flame Time (Seconds) | 0 | 0 |

In the vertical flame test on treated fabric after printing and before washing, each of the 15 specimens seamed in the length direction had "zero burn", i.e., all extinguished burn immediately upon retraction of the test flame. From 15 specimens seamed in the width direction, 2 specimens had self-extinguishing drips at 3, and 6 seconds, respectively. The remaining specimens showed "zero burn".

In the vertical flame tests on treated fabric after 50 washings, each of the 15 specimens seamed in the length direction had "zero burn". From 15 specimens seamed in the width direction, two specimens had self-extinguishing drips at 4 seconds. The remaining specimens showed zero burn.

What is claimed is:

1. The method of treating polyester textile materials to increase their fire resistant characteristics which comprises applying directly thereto a solution free from print binder, said solution containing at least 0.5% by weight of a water-soluble material selected from the group consisting of those having the structures

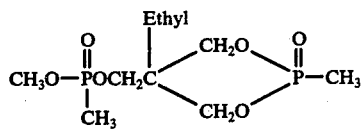

and

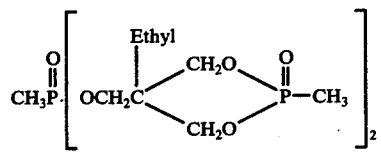

and mixtures thereof and
heating at a temperature of at least 250° F. to deposit on said textile materials from 0.5% to 15% of said material by weight.

2. The method as claimed in claim 1 in which the solution is aqueous.

3. The method as claimed in claim 1 in which the textile materials are 100% polyester.

4. The method as claimed in claim 3 in which the solution is aqueous.

5. The method as claimed in claim 4 in which the heating is carried out at a temperature of at least 340° F.

6. The method of making printed polyester fabrics by printing thereon a pigment print paste free from fire retardants having a coverage of at least 30% of the total fabric area wherein the improvement comprises applying directly to said fabrics before printing a solution, free from print binder, containing at least 0.5% by weight of a water-soluble material selected from the group consisting of those having the structures

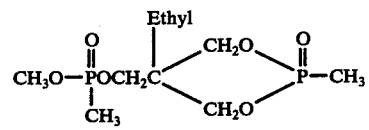

and

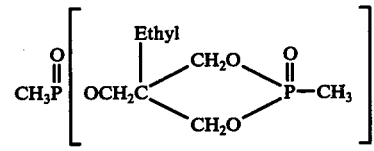

and mixtures thereof and
heating at a temperature of at least 250° F. to deposit on said fabrics from 0.5% to 15% of said material by weight.

7. The method as claimed in claim 6 in which said temperature is at least 340° F.

* * * * *